(12) United States Patent
Levin et al.

(10) Patent No.: US 9,101,313 B2
(45) Date of Patent: Aug. 11, 2015

(54) SYSTEM AND METHOD FOR IMPROVING A PERFORMANCE ESTIMATION OF AN OPERATOR OF A VEHICLE

(75) Inventors: Daniel Levin, Gothenburg (SE); Lena Westervall, Torslanda (SE); Gustav Markkula, Gothenburg (SE); Peter Kronberg, Karna (SE); Trent Victor, Vastra Frolunda (SE)

(73) Assignees: VOLVO CAR CORPORATION, Gothenburg (SE); VOLVO TECHNOLOGY CORPORATION, Gothenburg (SE)

( * ) Notice: Subject to any disclaimer, the term of this patent is extended or adjusted under 35 U.S.C. 154(b) by 6 days.

(21) Appl. No.: 13/601,844

(22) Filed: Aug. 31, 2012

(65) Prior Publication Data
US 2013/0073115 A1 Mar. 21, 2013

(30) Foreign Application Priority Data
Sep. 2, 2011 (EP) .................................... 11179798

(51) Int. Cl.
A61B 5/18 (2006.01)
G08B 21/06 (2006.01)
(Continued)

(52) U.S. Cl.
CPC . *A61B 5/18* (2013.01); *G08B 21/06* (2013.01); B60W 40/09 (2013.01); B60W 2040/0872 (2013.01); B60W 2540/10 (2013.01); B60W 2540/18 (2013.01); B60W 2550/308 (2013.01)

(58) Field of Classification Search
CPC ............ A61B 3/113; A61B 5/18; A61B 5/48; A61B 5/11; B60W 40/02; B60W 50/16; G08B 21/06; H04M 1/6083; H04M 1/72577; B60R 16/0231; G08G 1/096716; B60Q 9/00; G06F 8/76; G06Q 30/0283; G06Q 40/08; G09B 9/052
USPC .................... 701/1; 600/544, 558; 455/569.2; 340/436

See application file for complete search history.

(56) References Cited

U.S. PATENT DOCUMENTS 6,580,973 B2 * 6/2003 Leivian et al. .................... 701/1
6,974,414 B2 12/2005 Victor
(Continued)

FOREIGN PATENT DOCUMENTS

DE 102007046037 B3 4/2009
EP 2426001 3/2012
WO WO-2007090896 A1 8/2007

OTHER PUBLICATIONS

International Search Report.
(Continued)

*Primary Examiner* — Tuan C. To
*Assistant Examiner* — Yuri Kan
(74) *Attorney, Agent, or Firm* — Harness, Dickey & Pierce, P.L.C.

(57) ABSTRACT

System for improving a performance estimation of an operator of a vehicle, comprising a first module implementing a first method for estimating a performance state of vehicle operation, a second module implementing a second method for estimating at least one of a physiological and behavioral state of the operator, a device for sharing an estimated state between one of the first and the second module and the other one of the first and the second module, wherein the implemented estimation method of one of the first and the second module is adjusted based on the state of the other one of the first and the second module, thereby improving the estimation of at least one of the performance state of vehicle operation and the physiological and/or behavioral state of the operator.

19 Claims, 3 Drawing Sheets

(51) Int. Cl.
*B60W 40/09* (2012.01)
*B60W 40/08* (2012.01)

(56) References Cited

U.S. PATENT DOCUMENTS

| | | |
|---|---|---|
| 2003/0181822 A1* | 9/2003 | Victor ............................ 600/558 |
| 2004/0172172 A1* | 9/2004 | Kubota et al. ...................... 701/1 |
| 2005/0128092 A1 | 6/2005 | Bukman et al. |
| 2007/0027583 A1* | 2/2007 | Tamir et al. ........................ 701/1 |
| 2007/0124027 A1* | 5/2007 | Betzitza et al. .................... 701/1 |
| 2008/0113690 A1* | 5/2008 | Appleby .................... 455/569.2 |
| 2009/0115589 A1 | 5/2009 | Galley et al. |
| 2010/0007480 A1* | 1/2010 | Uozumi et al. ............... 340/436 |
| 2010/0241021 A1* | 9/2010 | Morikawa et al. ............ 600/544 |
| 2012/0173044 A1* | 7/2012 | Srinivasan et al. ................ 701/1 |

OTHER PUBLICATIONS

European Office Action dated Nov. 8, 2013 issued in corresponding European Application No. 11179798.1.

* cited by examiner

SYSTEM AND METHOD FOR IMPROVING A PERFORMANCE ESTIMATION OF AN OPERATOR OF A VEHICLE

PRIORITY STATEMENT

This claims priority under 35 U.S.C. §119 to European Patent Application No. 11179798.1, filed on Sep. 2, 2011, the contents of which is hereby incorporated by reference in its entirety.

FIELD OF THE INVENTION

The present invention relates to a system for improving a performance estimation of an operator of a vehicle, and more particularly to a system having two modules respectively estimating a performance state of vehicle operation and at least one of a physiological and behavioural state of the operator.

The invention also relates to a corresponding method for improving a performance estimation of an operator of a vehicle.

BACKGROUND OF THE INVENTION

Traffic accidents often occur due to driver impairment caused by, for example, drowsiness, illness, distraction, intoxication, etc. In order to prevent accidents caused by driver impairment, it may be vital to provide the driver with a warning message to re-establish the attention of the driver to the surrounding traffic situation, or in a critical situation to advice the driver to take a break or switch to another driver of the vehicle.

Several systems are known which attempt to predict the behaviour of the driver and provide the driver with a warning message in the event that he/she is not aware of the current driving situation or the environment of the vehicle. However, it may be vital to provide a warning message which the driver is capable to assimilate and react to. In other words, it may be vital to provide different warning messages for different causes of driver impairment. For example, a drowsy driver should be given a warning message intended for drowsiness and not a message intended for e.g. an intoxicated or distracted driver. A warning message intended for e.g. a distracted driver when the driver in fact is drowsy, may result in that the driver does not assimilate and react to the message in a correct and desired way.

U.S. Pat. No. 6,974,414 describes a system for monitoring the physiological behaviour of a driver. The system measures, for example, the driver's eye movement, eye-gaze direction, eye-closure amount, blinking movements, head movements, etc. A warning message is provided to the driver of the vehicle when the system detects one of a plurality of physiological behaviour that may cause an accident.

However, this system, as well as other known systems, may not discriminate well between the actual causes for the driver impairment, i.e. to specifically determine the casual factors behind a measured impairment. It is thus desirable to provide a system for improving performance estimation of the vehicle driver.

SUMMARY OF THE INVENTION

According to an aspect of the invention, the above may at least partly be met by a system for improving a performance estimation of an operator of a vehicle, comprising a first module implementing a first method for estimating a performance state of vehicle operation, a second module implementing a second method for estimating at least one of a physiological and behavioural state of the operator, and means for sharing an estimated state between one of the first and the second module and the other one of the first and the second module, wherein the implemented estimation method of one of the first and the second module is adjusted based on the state of the other one of the first and the second module, thereby improving the estimation of at least one of the performance state of vehicle operation and the physiological and/or behavioural state of the operator.

The invention is based on the understanding that by sharing e.g. an estimated state between the modules, the method executed by one or both of the modules may be adjusted to better perform its estimation. For example, the first module may only detect that an impaired driving performance takes place, which may be provided by currently known systems for detecting e.g. lane keeping, etc. The actual reason(s) and/or cause(s) of the impaired driving performance may not be discriminated well by solely the first module. However, by sharing, to the first module from the second module, an estimated state of the physiological and/or behavioural state of the operator, the first module may be given such information that a classification of the reason(s) and/or cause(s) of the impaired driving performance may be determined. It should be noted that the shared estimated state may also comprise sharing at least an intermediate estimated state between the modules, i.e. one of the modules may not necessarily share a "complete/full state estimation", but rather an intermediate state estimation, provided by for example one of the functional blocks of one of the state estimation methods. Hereby, when the first module has been provided with an indication from the second module of the causes of the impaired driving performance, an adjustment of the first method may be executed in order to improve its estimation. The system may, of course, also function the other way around, i.e. that the second module estimates a physiological and/or behavioural state of the operator and that the shared estimation from the first module provides the second module with such information that the second module may determine the actual factor(s) for the estimated physiological and/or behavioural state. Accordingly, it may, with the system according to the present invention, be possible to classify and determine a performance estimation of the operator. Moreover, to classify the estimation of one of the first and the second methods based on the estimation of the other one of the first and the second methods may provide a robust system which may be improved, compared to prior art systems, in order to estimate the cause(s) of an impaired driving performance. Hence, if the first method estimates a specific driving performance, the second method may provide its estimation as an input to the first module such that a classification of the estimation of the first method may be achieved. This is of course also possible the other way around as described above, i.e. that the estimation of the first method is provided as an input to the second module for classifying the detection of the second method.

According to a further example, drowsy driving performance is a slow process, on the minute-scale, while distracted driving is a fast process, on the second-scale. The algorithm of the first method may therefore, based on the received estimation from the second module, be adapted to work on the minute-scale or on the second-scale. This may be advantageous when, for example, the second module detects distracted driving. Hereby, the algorithm of the first module may be arranged to work on the second-scale and filter out driving behaviour which may be typical for e.g. drowsy driving behaviour, which works on the minute scale as described above. Hence, when the second module provides its estimation to the first module, the first method of the first module may adjust the time horizon of its algorithm.

Moreover, when providing a state estimation from e.g. the second module to the first module, the first module may be further arranged to seek for the driving behaviour estimated by the second module, in order to secure that the estimation of the second module is correct. For example, if the second module detects drowsy driving performance, the algorithm of the first module may be arranged to work on the minute scale to find indication of drowsy driving.

Such a system may, furthermore, also be beneficial in vehicle warning systems, where it may be essential to provide the operator of the vehicle with a warning message. Hence, a specific warning signal/message may also be provided to the operator of the vehicle, which signal/message is adapted for the estimated cause(s) of the impaired driving.

The wordings "performance estimation" should in the following be interpreted as an estimation of the cause(s) of an impaired driving, i.e. the cause(s) of a certain behaviour of the operator of the vehicle.

The wording "first module" and "second module" should be understood to mean sub systems (physical devices, programmable functional blocks, etc.) which are arranged to receive data from internal and external sensors/detectors which acquires data from the interior and/or the exterior of the vehicle, respectively. Based on the received data, the modules provide estimation(s) of the performance state of vehicle operation and physiological and behavioural state of the operator, respectively.

Three exemplary embodiments are described below for implementing sharing of the estimated state between one of the first and the second module and the other one of the first and the second module.

In the first exemplary sharing implementation, the first method of the first module estimates a performance state of the vehicle operation, based on the received data from the external sensor(s)/detector(s). The second method of the second module estimates at least one of a physiological and behavioural state of the operator, based on the received data from the internal sensor(s)/detector(s). The second module then provides the first module with its estimated state, i.e. the second module share its estimation to the first module. The first method of the first module is thereafter adjusted based on the received estimation of the second method.

In the second exemplary sharing implementation, the estimation is shared in the opposite "direction" compared to the first sharing implementation. Hence, the first and the second method provide their respective estimation as described above, and thereafter the first module provides the second module with its estimated state, i.e. the first module share its estimation to the second module. The second method of the second module is thereafter adjusted based on the received estimation of the first method.

In the third exemplary sharing implementation, the first method shares its estimated state to the second module and the second method shares its estimated state to the first module, i.e. the sharing is provided in both "directions". In this case, the estimated states of the first and the second method may be adjusted for a predetermined number of sharing cycles. For example, when the second method has adjusted its estimated state based on the received estimation of the first method, the second method may share its new estimated state to the first method, which adjusts its estimation. The first method may then again provide the second method with an updated estimation or, if the system finds the estimation reliable enough, output the performance estimation to e.g. the vehicle warning system or a Human Machine Interface (HMI) of the vehicle.

It should however be noted that the performance estimation does not necessarily have to be given as output from solely one of the first and the second modules, estimations may also be given as output from both modules to the warning system or HMI of the vehicle. Moreover, the outputted estimation may also be a combination of the two modules by weighing each of the estimation compared to a confidence value prior to providing the estimation to the warning system or HMI of the vehicle.

According to an embodiment of the present invention, the first method may be arranged to detect at least one of a vehicle lane-keeping, vehicle speed, vehicle distance-keeping and vehicle steering behaviour. Hereby, the first method may detect if the operator of the vehicle is operating the vehicle in a manner which may be caused by operator impairment. For example, an impairment of the vehicle operator may likely have occurred if the vehicle is drifting from one side of the lane to the other, uncontrollably accelerating/decelerating, or exhibits poor distance keeping ability to lead vehicles. The first method may however also be arranged to detect further vehicle behaviour, such as inexact steering, slow reaction time to traffic changes, braking directly followed by pressing the accelerator pedal, various steering wheel movement patterns, etc. Moreover, the first method may acquire information for detection of the operating performance state of the vehicle by e.g. camera(s), radar, GPS, vehicle-to-vehicle communication, vehicle-to-infrastructure communication, etc.

Furthermore, the second method may be arranged to detect at least one of an operator eye-gaze direction, operator head movements, body movements and operator eye-lid behaviour. Hence, the second method detects the operator of the vehicle, and in particular the physiological and/or behavioural state of the operator. It should however be noted that the second method may also be arranged to detect a plurality of other physiological or behavioural states of the operator, for example interaction with various vehicle systems such as the radio or the climate control system, interaction with other passengers, voice pattern, speech recognition, response/reaction to triggered events, changes in different skin parameters, breath or ambient air alcohol content, pupil responses, heart rate, etc. Moreover, the second method may acquire information for detection of physiological and/or behavioural state of the operator by e.g. camera(s), audio recognition, button presses, EKG, etc.

According to an embodiment of the present invention, the first module may comprise a plurality of predefined methods, wherein each of the predefined methods is arranged to detect a specific driving performance state of the operator. Each of the plurality of predefined methods is hereby fine-tuned to detect a specific driving performance state of the operator. An advantage is that a more sophisticated system may be arranged, where each one of the predefined methods may be provided with algorithm(s) that are specifically designed to detect a certain driving performance state of the operator. Moreover, the selection of one of the plurality of predefined methods may be based on the estimation of the second module. Hereby, the estimation of the second module may be given as input to the first module, such that the first module can determine which one of the plurality of predefined methods to be selected. The second and third exemplary sharing implementations, as described in detail above, are of course also valid for this embodiment of the invention.

For example, the predefined methods may be provided with lane keeping algorithms having various time horizons as described above, i.e. on the minute-scale or on the second-scale, or algorithms for detecting various vehicle maneuvers. Furthermore, the predefined methods may be provided with algorithms for detecting steering-wheel movement patterns or speed keeping patterns, etc. Still further, the predefined method may also use combinations of the above described algorithms.

Furthermore, the first module may comprise a weighing means arranged to receive the plurality of driving performance states and weight an estimated driving performance based on the estimation of the second module. Hereby, the algorithms for each of the plurality of predefined methods are running in parallel and provided to the weighing means. The weighing means may, for example, be provided with various weighing parameters based on the estimation received from the second module. The weighing parameters may use linear or non-linear calculations, such as square root calculations, logarithmic functions, etc. The second module provides the estimation from the second method to the first module such that the weighing means can estimate the current cause of the driving performance of the operator. In other words, the weighing means classifies the driving performance state based on the plurality of driving performance states and the estimation of the second module. The second and third exemplary sharing implementations are valid also for this embodiment of the invention but the sharing may also be provided between the weighing means and the second module. Moreover, the detected driving performance state of the operator may be one of drowsiness/fatigue, distraction, illness, intoxication, at-risk driving behaviour and poor driving. An advantage of a classification of the various performance state of the operator is, as discussed above, to be able to more precisely detect the cause of driver impairment. This may provide e.g. warning systems of the vehicle with information such that the warning systems can be able to provide the operator of the vehicle with a warning signal/message that he/she can assimilate and properly react to.

According to another aspect of the present invention, there is provided a method for improving a performance estimation of an operator of a vehicle, the vehicle comprising a system having a first module implementing a first method for estimating a performance state of vehicle operation, and a second module implementing a second method for estimating at least one of a physiological and behavioural state of the operator, wherein the method comprises the steps of receiving sensor data to the first module for estimation of the performance state of vehicle operation, receiving sensor data to the second module for estimation of at least one of a physiological and behavioural state of the operator, sharing the estimated state between one of the first and the second module and the other one of the first and the second module, and adjusting the implemented method of one of the first and the second module based on the estimation of the other one of the first and the second module, thereby improving the estimation of at least one of the performance state of vehicle operation and the physiological and/or behavioural state of the operator. This aspect of the invention provides similar advantages as discussed above in relation to the previous aspect.

According to a still further aspect of the invention there is provided a computer readable medium embodying a computer program product for improving a performance estimation of an operator of a vehicle, the vehicle comprising a system having a first module implementing a first method for estimating a performance state of vehicle operation and a second module implementing a second method for estimating at least one of a physiological and behavioural state of the operator, the computer program product comprising code configured to, when executed by a processor receiving sensor data to the first module for estimation of the performance state of vehicle operation, receiving sensor data to the second module for estimation of at least one of a physiological and behavioural state of the operator, sharing the estimated state between one of the first and the second module and the other one of the first and the second module, and adjusting the implemented method of one of the first and the second module based on the estimation of the other one of the first and the second module, thereby improving the estimation of at least one of the performance state of vehicle operation and the physiological and/or behavioural state of the operator. Also this aspect of the invention provides similar advantages as discussed above in relation to the previous aspects of the invention.

Other objectives, features and advantages of the present invention will appear from the following detailed disclosure, from the attached dependent claims as well as from the drawings.

BRIEF DESCRIPTION OF THE DRAWINGS

These and other aspects of the present invention will now be described in more detail, with reference to the appended drawings showing exemplary embodiments of the present invention, wherein.

DETAILED DESCRIPTION OF PREFERRED EMBODIMENTS

Figure 1:
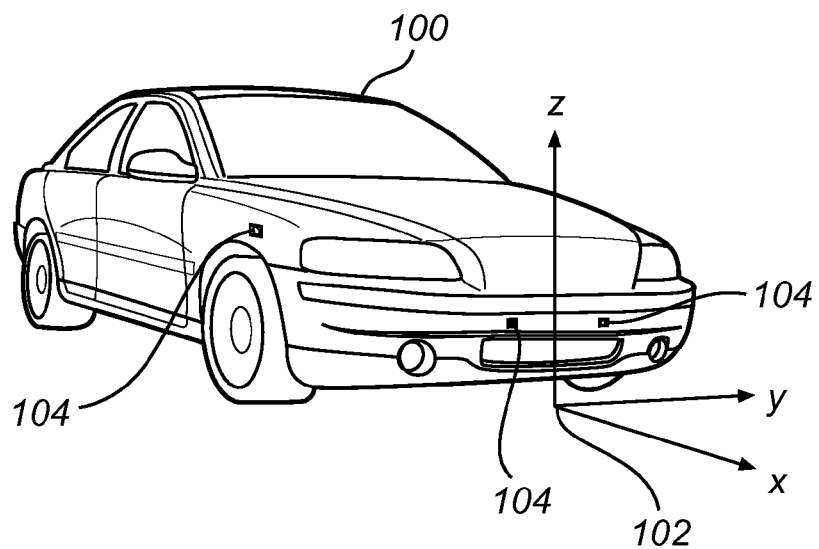
FIG. 1 is a perspective view of a vehicle equipped with external sensors and a coordinate system at its front end.

The present invention will now be described more fully hereinafter with reference to the accompanying drawings, in which exemplary embodiments of the invention are shown. This invention may, however, be embodied in many different forms and should not be construed as limited to the embodiments set forth herein; rather, these embodiments are provided for thoroughness and completeness. Like reference characters refer to like elements throughout.

In the following, the present invention is described with reference to a system for improving a performance estimation of an operator of a vehicle. The vehicle is preferably equipped with interior sensor(s) for retrieving information of the vehicle operator and external sensor(s) for retrieving information of the vehicle operation as well as the surrounding environment of the vehicle. For the sake of better understanding, the internal and external sensors will now be described in relation to FIGS. 1-3.

FIG. 1 shows an exemplary vehicle, here illustrated as a car 100, in which a system according to the present invention may be incorporated. The car 100 is provided with external sensors 104 arranged to detect vehicle operation, such as overtaking, vehicle speed, vehicle yaw rate, etc, as well as the surrounding environment of the vehicle, e.g. lane markings, road marks, road curves, surrounding vehicles, etc. The external sensors 104 may be e.g. cameras or radar sensors. Preferably, a combination of camera and radar sensors may be used, since the camera provides a high precision when determining the height and width of an object, whereas a radar sensor provides a high precision when determining the distance to the object. Hereby, size, position, speed, etc. of the surrounding object can be determined. With reference to the position of the car 100, a coordinate system 102, here illustrated as a Cartesian coordinate system, is located at the front end of the car 100. The coordinate system 102 is arranged to follow the vehicle and the axis represent the longitudinal direction (x-axis), lateral direction (y-axis) and vertical direction (z-axis), respectively. The detected objects, in conjunction with the coordinate system 102 of the car 100, are provided to a system of the vehicle such that the system can determine the size and position of the object relative to the car 100. As the system is continuously provided with the detected objects from the different sensors 104, it is also possible to determine speed and acceleration of surrounding traffic environment.

Figure 2:
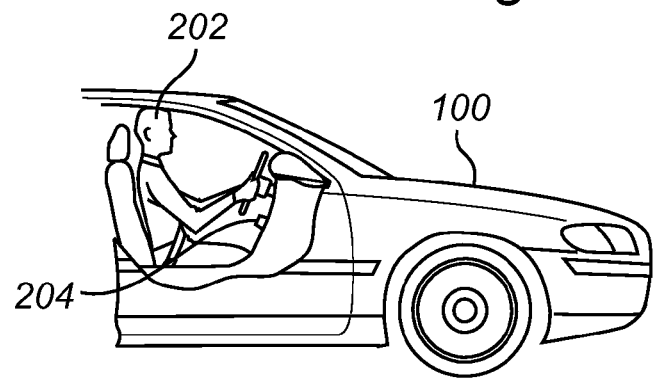
FIG. 2 is a perspective view of the interior of the vehicle, equipped with an internal sensor.
Figure 3:
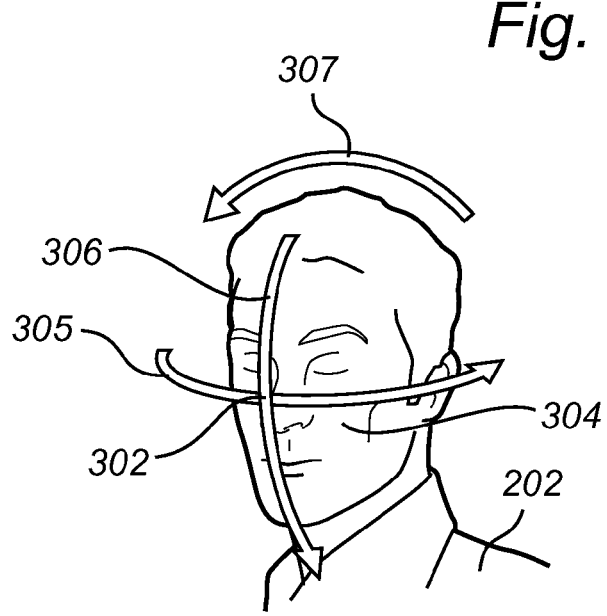
FIG. 3 illustrates a coordinate system of the face of a vehicle operator.

FIG. 2 illustrates an interior of the car 100 including a vehicle operator 202, wherein the car 100 is equipped with an internal sensor, here illustrated as a camera system 204. The camera system 204 is arranged to determine the behaviour of the vehicle operator 202 during vehicle operation. Furthermore, the camera system 204 may be arranged to focus on a predetermined number of positions of the operator's face. These positions may, for example, be the eyes, eye-lids, eyebrows, nose, mouth, cheek, etc. The camera system 204 may be pre-calibrated for a specific operator 202 normally operating the car 100 or being calibrated each time an operator 202 enters the driver seat of the car 100. As the camera system 204 has detected the different positions of the operator's face, an estimation of facial behaviour is possible. The camera system 204 may hence detect, e.g. head and eye direction, head pose, eye saccade, head-eye saccade, eye closure, speed of eye closure, etc. The camera system 204 may also, by use of a coordinate system 302 in connection to the operator's face 304, illustrated in FIG. 3, detect if the head of the operator is rotating to the right or left (yaw) 305, rotating up or down (pitch) 306 or leaning towards the right or left shoulder (roll) 307. The coordinate system 302 of the face 304 is preferably a polar coordinate system with its origin positioned between the eyes of the operator.

Furthermore, the internal sensors may also, instead of, or additionally to the camera system 204, include other type of operator detecting means. This may, for example, include sensors for detecting EKG or EEG of the operator, steering wheel sensors for detection of steering behaviour, sensors in the acceleration pedal and/or braking pedal for detection of inconsistent acceleration and/or braking of the car 100, sensors in various buttons of the car 100 to detect if, for example, the operator 202 is adjusting any of the various functionalities of the infotainment system, etc. A still further internal sensor may be a breath analysis sensor or pupil size sensor for detecting intoxication of the operator 202.

Figure 4:
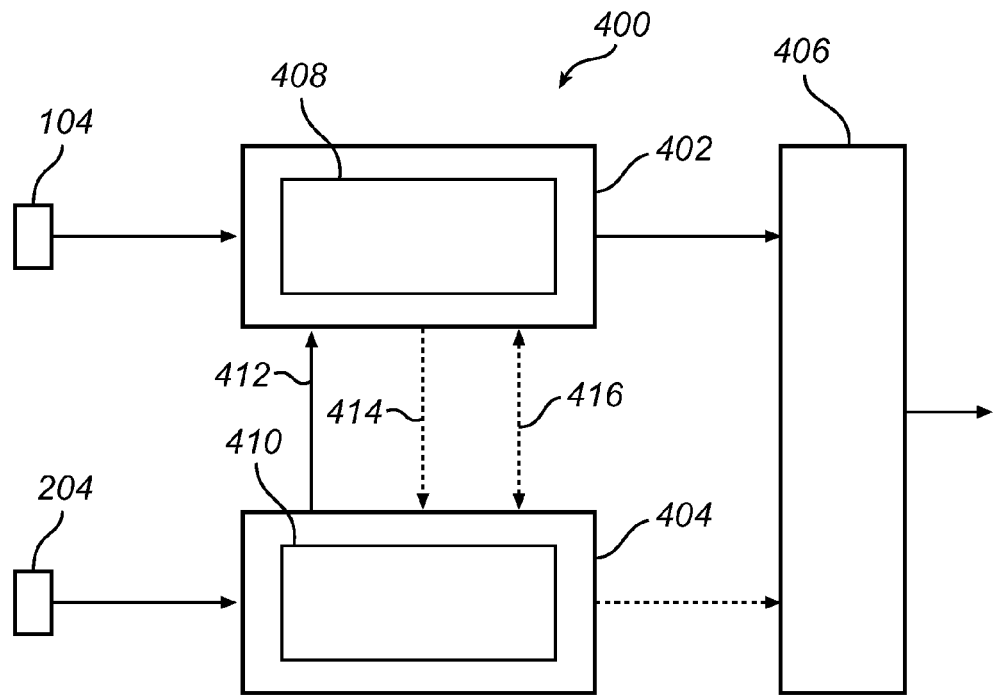
FIG. 4 illustrates an embodiment of the system according to the present invention, having a first and a second module and an HMI.

Now referring to FIG. 4, which illustrates an exemplary embodiment of a system according to the present invention. The system 400 comprises a first module 402 and a second module 404, wherein at least one of the modules, in the illustrated embodiment, is connected to an e.g. Human Machine Interface (HMI) 406 or the like. In the exemplary embodiment of FIG. 4, the first module 402 is connected to the HMI 406, while the second module 404 is able to be connected to the HMI 406, illustrated with a dashed line. The first module 402 is, in the illustrated embodiment, a system arranged to estimate a performance state of vehicle operation, i.e. the current driving performance of the vehicle operator 202. Moreover, the first module 402 comprises a first method 408 having driving performance estimation algorithms for detecting the performance state of vehicle operation. The performance state of vehicle operation should be understood to mean certain behaviour of the car 100 during operation, for example, vehicle lane-keeping, vehicle speed, vehicle distance keeping and vehicle steering behaviour. These are, however, not limited to the scope of the invention which is also applicable for any other type of driving performance of the operator 202. Furthermore, in order for the first method 408 to estimate the performance state of vehicle operation, the external sensor(s) 104 provides the first module 402 with the sensor data as described above in relation to FIG. 1.

Still further, the second module 404 is, in the illustrated embodiment, a system arranged to estimate physiological and behavioural state(s) of the vehicle operator 202, i.e. to detect and estimate any changes in physiological and behavioural state of the operator 202. The estimation of physiological and behavioural state(s) of the operator is provided by a second method 410 implemented in the second module 404, which receives sensor data from the internal sensor(s) described above in relation to FIGS. 2 and 3. Examples of physiological and behavioural states estimated by the second module may, for instance, include estimation of eye-gaze direction, facial gaze direction, interaction with vehicle systems, eye-closure duration, eye-closure speed, eye-opening speed, conversation with other passenger(s) of the vehicle, estimation of EEG and/or EKG, response/reaction time to triggered event(s), etc.

As also illustrated in FIG. 4, the first 402 and second modules 404 are connected to each other in order to share the estimation(s) provided by the respective methods. There are, in the exemplary embodiment, illustrated three different sharing implementations 412, 414, 416, where the first sharing implementation 412 provides the physiological and/or behavioural state(s) estimated by the second module 404 to the first module 402. In the second sharing implementation 414 the performance state of vehicle operation estimated by the first module 402 is shared to the second 404 module, and in the third sharing implementation 416 the estimations provided by the first 402 and the second modules 404 are shared between each other, i.e. the third sharing implementation 416 is a combination of the first 412 and the second 414 sharing implementations. The third sharing implementation 416 may also be an iterative process where the estimations of the first 402 and the second 404 modules are continuously updated and adjusted based on the estimation of the other one of the first 402 and the second 404 modules. The exemplary sharing implementations will now be described more detailed.

In the first exemplary sharing implementation 412, the first method 408 of the first module 402 estimates a performance state of the vehicle operation and the second method 410 of the second module 404 estimates at least one of a physiological and behavioural state(s) of the operator, as described above. The second module 404 provides the first module 402 with its estimated state, i.e. the second module 404 shares its estimation to the first module 402. The first method 408 of the first module 402 is thereafter adjusted based on the received estimation of the second method 410. For example, if the first module 402 estimates a current driving performance of the car 100, e.g. inconsistent lane keeping, it may not be able to solely determine the actual reason(s) and/or cause(s) of that driving performance. When, however, the second module 404 shares its estimated state to the first module 402, the first method 408 of the first module 402 may be adjusted such that a classification of the reason(s) and/or cause(s) of the impaired driving performance, i.e. the inconsistent lane keeping, may be determined. According to yet another example of the embodiment of the first sharing implementation, if the second module 404 detects that the operator 202 of the car 100 has slow eye-closure speed in combination with longer periods of closed eye lids, the second module 404 may provide the first module 402 with an estimation of eye-lid behaviour of the operator 202. As the first module 402 has received the estimation from the second module 404, the first module 402 may be adapted to estimate various performance state of vehicle operation that may occur due to, in this example, the specific eye-lid behaviour of the operator 202. If the first module 402 detects such a state of vehicle operation, for example inconsistent lane-keeping on the minute-scale, an estimation and classification of drowsiness or fatigue can be made. Thereafter, the first module 402 may provide e.g. the warning system or HMI 406 of the vehicle with the estimated classification to provide the operator 202 with a suitable warning message/signal. As an example, a loud and clear message to the operator 202 that he/she should take a rest.

In the second exemplary sharing implementation 414, the estimation is shared in the "opposite direction" compared to the first sharing implementation 412. Hence, the first 408 and the second 410 method provides their respective estimation as described above, and thereafter the first module 402 provides the second module 404 with the estimated state of the first method 408, i.e. the first module 402 shares its estimation to the second module 404. The second method 410 of the second module 404 is thereafter adjusted based on the received estimation of the first method 408. Hereby, the second method 410 may be able to determine the actual cause(s)/reason(s) for the specific physiological and/or behavioural state initially estimated by the second method 410. Also, for example, if the first module 402 provides the second module 404 with an estimation of inconsistent steering behaviour and inconsistent acceleration and braking, the second module 404 may be adjusted to detect and estimate, for example, intoxication of the operator 202. If the second module 404 detects such behaviour, the second module 404 may e.g. provide the warning system or HMI 406 of the car 100 with an estimated classification to provide the operator 202 with a suitable warning message/signal.

In the third exemplary sharing implementation 416, the first module 402 shares its estimated state to the second module 404 and the second module 404 shares its estimated state to the first module 402, i.e. the sharing is provided in both "directions". In this case, the estimated states of the first 402 and the second 404 module may be adjusted for a predetermined number of sharing cycles. For example, if the first module 402 estimates an inconsistent lane-keeping, the second module 404 may be adapted to estimate causes of such inconsistent lane-keeping. The second module 404 then, for instance, detects and estimates button presses on the infotainment system of the car 100 in combination with an eye-gaze of the operator directed towards the infotainment system. The second module 404 may then provide the first module 402 with its established estimation. The first method 408 may then be adapted to e.g. estimate surrounding objects of the car 100 in order to determine the likeliness of e.g. an accident to occur. If a surrounding object is being approached, the first module 402 may thereafter provide the second module 404 with this estimation such that the second module 404 may determine and estimate if the eye-gaze of the operator 202 is towards the approached object or not. The first 402 and/or second 404 module may then, depending on the criticality of the situation, provide e.g. the warning system or HMI 406 of the car 100 with a classification of the performance estimation of the operator 202 such that a suitable warning message/signal is provided to the vehicle operator 202.

It should be noted that the estimation of each of the modules 402, 404 may be updated with various time intervals. For example, a car 100 driving at a high speed on a curvy road may be updated more frequently than a car 100 driving at a low speed on a straight road, i.e. the modules 402, 404 provides estimation of vehicle operation and physiological and behavioural state more frequently.

Figure 5:
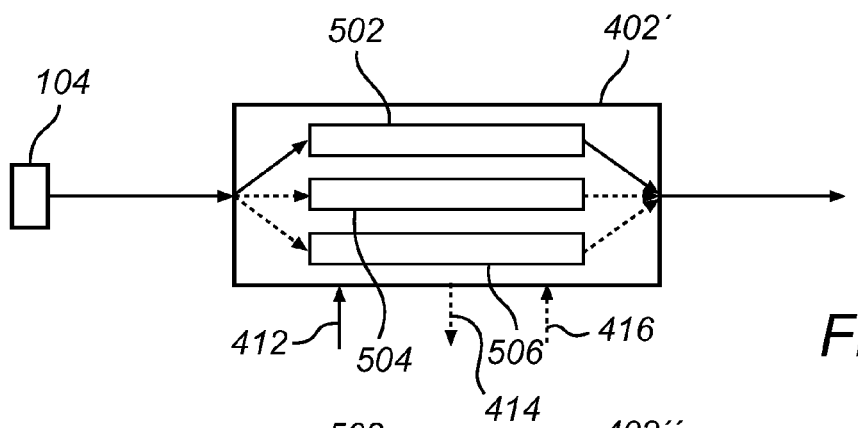
FIG. 5 illustrates an embodiment of the first module according to the embodiment illustrated in FIG. 4.
Figure 6:
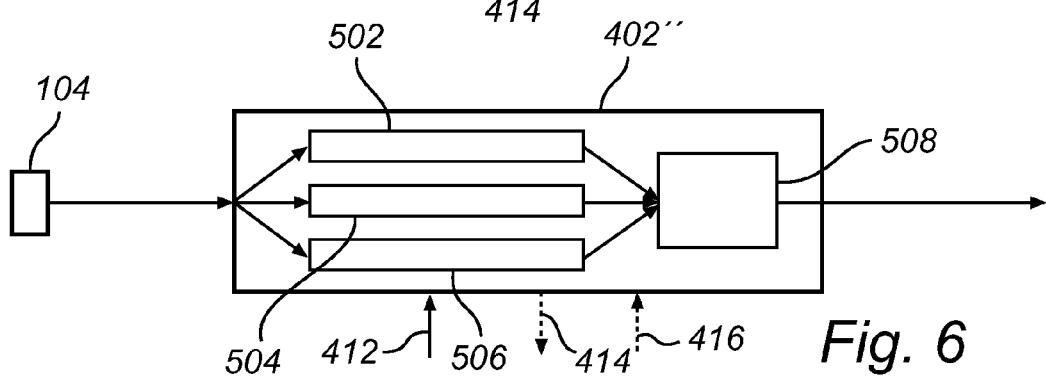
FIG. 6 illustrates yet another embodiment of the first module according to the embodiment illustrated in FIG. 4, and FIG. 7 provides a flowchart of an embodiment of a method for utilizing the system illustrated in FIGS. 4-6.
Figure 7:
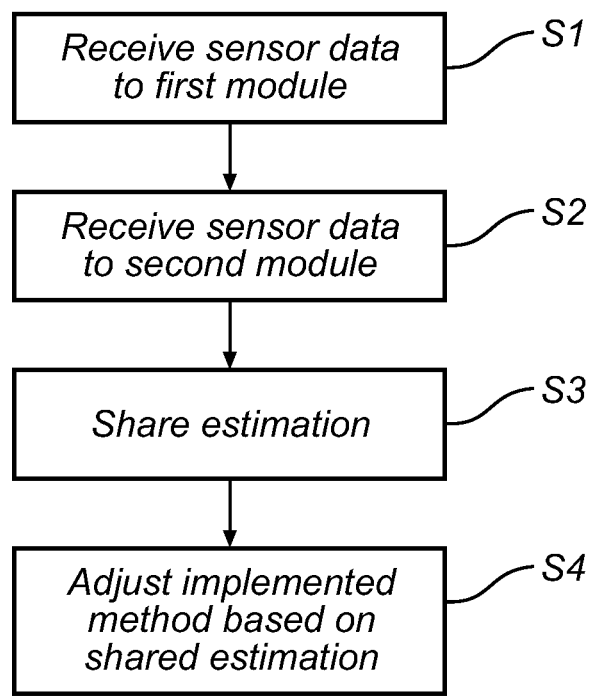

FIGS. 5 and 6 illustrate two different embodiments of the first module 402', 402" according to the present invention, which will be described in the following. It should be noted that the exemplary sharing implementations 412, 414, 416 described above in relation to FIG. 4 are equally applicable for the embodiments of FIGS. 5 and 6 and will therefore not be described further unless there are differences needed to be described.

According to FIG. 5, the first module 402' comprises a plurality of predefined methods 502, 504, 506, each arranged with algorithm(s) for detecting specific driving performance(s) of the operator 202. In the embodiment of FIG. 5, three predefined methods 502, 504, 506 are illustrated but the invention is, of course, equally applicable with more or less predefined methods if desired. Each of the predefined methods 502, 504, 506 is arranged to detect a specific driving performance of the operator 202, such as drowsy driving, distracted driving, intoxicated driving, at-risk driving, poor driving, etc. When, for example, the first exemplary sharing implementation 412 is provided by the system 400, the first module 402' receives the estimation provided by the second module 404 as described above. Depending on the specific estimation of the second module 404, one of the predefined methods 502 is selected such that the first module 402' utilizes the algorithm(s) of that predefined method 502 to estimate the performance state of vehicle operation. The selected predefined method 502 is illustrated in FIG. 5 as a method for detecting drowsy driving, but may be any other method suitable for detecting other performance state of the vehicle operator 202 as well.

Now referring to FIG. 6 illustrating yet another embodiment of the first module 402" according to the present invention, which will be described in relation to the first exemplary sharing implementation 412 as described above. The embodiment of FIG. 6 also comprises a plurality of predefined methods 502, 504, 506 as described above in relation to FIG. 5. Furthermore, in the embodiment of FIG. 6, the first module 402' also comprises a weighing device 508, which is arranged to receive the algorithms for the plurality of predefined methods 502, 504, 506. Hereby, the plurality of predefined methods 502, 504, 506 are running in parallel and the weighing device 508 weights an estimated driving performance of the vehicle operator 202 based on the received estimation by the second module 404. For example, if the second module 404 estimates operator eye-lid behaviour, e.g. slow speed of eye-closure/eye-opening, the weighing device 508 may for instance weight that the first module 402" should mainly detect drowsy driving performance (e.g. 70-80%), but also intoxicated driving performance (e.g. 20-30%).

Although the embodiments illustrated in FIGS. 5 and 6 are described in relation to the first exemplary sharing implementation 412, it should be noted that they are equally applicable using the second 414 and third 416 exemplary sharing implementations as well. According to the embodiment of FIG. 6, the sharing may be provided between the weighing device 508 of the first module 402" and the second module 404 as well as between both of the modules 402", 404 as described above.

In the claims, the word "comprises" does not exclude other elements or steps, and the indefinite article "a" or "an" does not exclude a plurality. A single computer or other unit may fulfil the functions of several items recited in the claims. The mere fact that certain measures are recited in mutually different dependent claims does not indicate that a combination of these measured cannot be used to advantage.

The invention has mainly been described above with reference to a few embodiments. However, as is readily appreciated by the skilled addressee, other embodiments than the ones disclosed above are equally possible within the scope of the invention, as defined by the appended patent claims. For example, the invention is also applicable for trucks, buses, dumpers, wheel loaders and other type of vehicles than the above described car. Also, the invention is not limited to the use of a camera and/or radar sensor for detecting the environment of the vehicle; other known and suitable sensors are of course also valid. It is also possible to use more than two modules, for example, a third module arranged to detect various traffic conditions such as density, speed of surround vehicles, current weather condition, etc may also be provided to the above system.

The invention claimed is:

1. A system for improving a performance estimation of an operator of a vehicle, comprising:
   a processor, including,
   a first module configured to implement a first method for estimating a performance state of vehicle operation, and
   a second module configured to implement a second method for estimating at least one of a physiological state of the operator and a behavioural state of the operator,
   wherein the processor is configured to provide the estimated state of the first module to the second module and to provide the estimated state of the second module to the first module,
   wherein each one of the first module and the second module is configured to adjust an associated method for estimating based on the estimated state provided from the other one of the first module and the second module to improve the estimation of at least one of the performance state of vehicle operation, the physiological state of the operator, and the behavioural state of the operator, and
   wherein the processor is configured to generate a signal based on the improved estimation.

2. The system according to claim 1, wherein the first method detects at least one of a vehicle lane-keeping, vehicle speed, vehicle distance-keeping, and vehicle steering behaviour.

3. The system according to claim 1, wherein the second method detects at least one of an operator eye-gaze direction, operator head movements, operator eye-lid behavior and body movements.

4. The system according to claim 1, wherein the first module is configured to implement a plurality of methods, wherein each of the methods detects a specific driving performance state from among a plurality of driving performance states of the operator.

5. The system according to claim 4, wherein the first module is configured to select one of the plurality of methods based on the estimation of the second module.

6. The system according to claim 4, wherein the first module further comprises:
   a weighing device configured to receive the plurality of driving performance states and weigh an estimated driving performance based on the estimation of the second module.

7. The system according to claim 4, wherein the detected driving performance state of the operator is one of drowsiness/fatigue, distraction, intoxication, at-risk driving behavior, and poor driving.

8. A method for improving a performance estimation of an operator of a vehicle, the vehicle comprising a system including a processor having a first module and a second module, the first module being configured to implement a first method for estimating a performance state of vehicle operation, and the second module being configured to implement a second method for estimating at least one of a physiological and behavioural state of the operator, the method comprising:
   receiving, by the first module, sensor data for estimation of the performance state of vehicle operation;
   receiving, by the second module, sensor data for estimation of at least one of a physiological state of the operator and a behavioural state of the operator;
   providing, by the processor, the estimated state of the first module to the second module and providing, by the processor, the estimated state of the second module to the first module;
   adjusting, by the processor, the implemented method of one of the first module and the second module based on the estimation provided from the other one of the first module and the second module to improve the estimation of at least one of the performance state of vehicle operation, the physiological state of the operator, and the behavioural state of the operator; and
   generating, by the processor, a signal based on the improved estimation.

9. The method according to claim 8, wherein the sensor data for estimation of the performance state of vehicle operation includes data relating to at least one of a vehicle lane-keeping, vehicle speed, vehicle distance-keeping, and vehicle steering behaviour.

10. The method according to claim 8, wherein the sensor data for estimation of at least one a physiological and behavioural state of the operation includes data relating to at least one of an operator eye-gaze direction, operator head movements, operator eye-lid behaviour and body movements.

11. The method according to claim 8, wherein the first module is configured to implement a plurality of methods, wherein each of the methods detects a specific driving performance state of the operator from among a plurality of driving performance states of the operator.

12. The method according to claim 11, further comprising:
   selecting one of the plurality of methods based on the estimation of the second module.

13. The method according to claim 11, further comprising:
   receiving, by a weighing device, the plurality of driving performance states; and
   weighing, by the weighing device, an estimated driving performance based on the estimation of the second module.

14. A non-transitory computer readable medium including a computer program product for improving a performance estimation of an operator of a vehicle, the vehicle comprising a system including a processor having a first module and a second module, the first module being configured to implement a first method for estimating a performance state of vehicle operation, and the second module being configured to implement a second method for estimating at least one of a physiological state of the operator and a behavioural state of the operator, the computer program product comprising code to, when executed by the processor, cause the processor to:

receive sensor data from the first module for estimation of the performance state of vehicle operation;

receive sensor data from the second module for estimation of at least one of the physiological state of the operator and the behavioural state of the operator;

provide the estimated state of the first module to the second module and provide the estimated state of the second module to the first module;

adjust the implemented method of one of the first module and the second module based on the estimation provided from the other one of the first module and the second module to improve the estimation of at least one of the performance state of vehicle operation, the physiological state of the operator, and the behavioural state of the operator; and generate a signal based on the improved estimation.

15. The method according to claim 8, wherein the adjusting adjusts at least the implemented method of the first module based on the provided estimated state of the second module.

16. The non-transitory computer readable medium according to claim 14, wherein the computer program product further comprises code to, when executed by the processor, cause the processor to:

adjust at least the implemented method of the first module based on the provided estimated state of the second module.

17. The system according to claim 1, wherein the processor is configured to generate a warning message based on the signal.

18. The method according to claim 8, further comprising: generating a warning message based on the signal.

19. The non-transitory computer readable medium according to claim 14, wherein the computer program product further comprises code to, when executed by the processor, cause the processor to:

generate a warning message based on the signal.

* * * * *